(12) United States Patent
Rabinovich et al.

(10) Patent No.: US 9,389,155 B1
(45) Date of Patent: Jul. 12, 2016

(54) FATIGUE TEST SPECIMEN

(71) Applicant: United Technologies Corporation, Hartford, CT (US)

(72) Inventors: Albert Rabinovich, West Hartford, CT (US); Neil E. Anderson, Berlin, CT (US); William P. Ogden, Glastonbury, CT (US)

(73) Assignee: United Technologies Corporation, Farmington, CT (US)

( * ) Notice: Subject to any disclaimer, the term of this patent is extended or adjusted under 35 U.S.C. 154(b) by 265 days.

(21) Appl. No.: 14/097,509

(22) Filed: Dec. 5, 2013

Related U.S. Application Data

(60) Provisional application No. 61/777,351, filed on Mar. 12, 2013.

(51) Int. Cl.
| | |
|---|---|
| *G01N 33/00* | (2006.01) |
| *G01N 3/02* | (2006.01) |
| *G01N 3/62* | (2006.01) |
| G01N 3/08 | (2006.01) |
| C23C 8/20 | (2006.01) |
| G01N 3/32 | (2006.01) |

(52) U.S. Cl.
CPC .. *G01N 3/02* (2013.01); *G01N 3/62* (2013.01); *C23C 8/20* (2013.01); *G01N 3/08* (2013.01); *G01N 3/32* (2013.01); *G01N 2203/0005* (2013.01); *G01N 2203/0017* (2013.01); *G01N 2203/0266* (2013.01); *G01N 2203/0274* (2013.01)

(58) Field of Classification Search
CPC ............. G01N 3/08; G01N 3/32; G01N 3/62; G01N 2203/0017; G01N 2203/0005; G01N 2203/0274; G01N 2203/0266; C23C 8/20

USPC .............. 73/808, 810, 826, 866, 856; 148/27, 148/206, 215–216, 233, 235
See application file for complete search history.

(56) References Cited

U.S. PATENT DOCUMENTS

| 2,697,375 | A | * | 12/1954 | Brisack | ............... | F16B 19/1063 |
|---|---|---|---|---|---|---|
| | | | | | | 411/54 |
| 2,974,558 | A | * | 3/1961 | Hodell | ................ | F16B 19/1036 |
| | | | | | | 411/339 |
| 3,742,602 | A | * | 7/1973 | Brumwell | ................ | B25G 1/00 |
| | | | | | | 30/340 |
| 4,152,177 | A | * | 5/1979 | Mantel | ....................... | C23C 8/22 |
| | | | | | | 148/235 |
| 5,032,356 | A | * | 7/1991 | Kumagai | ............. | B23D 61/127 |
| | | | | | | 420/105 |
| 5,305,645 | A | * | 4/1994 | Reifsnider | ................ | G01N 3/32 |
| | | | | | | 73/808 |

(Continued)

OTHER PUBLICATIONS

Morita et al. "Effect of Titanium-Fine-Particle Bombaring Treatment on Corrosion Resistance of Aluminium Alloy and Carbon Steel". Transactions of the Japan Society of Mechanical Engineers Series A, vol. 77 (2011) No. 780. p. 1331-1339. <https://www.jstage.jst.go.jp/article/kikaia/77/780/77_780_1331/_pdf>.*

(Continued)

*Primary Examiner* — Lisa Caputo
*Assistant Examiner* — Jonathan Dunlap
(74) *Attorney, Agent, or Firm* — Bachman & LaPointe, P.C.

(57) ABSTRACT

A metallic test specimen (20) extends along a central longitudinal axis (500) between a first end (22) and a second end (24). The specimen has a first mounting section (30) and a section mounting section (32). A narrowed gauge section (34) is between the first mounting section and the second mounting section. The first mounting section and the second mounting section each have a blind compartment (44) extending longitudinally inward to a closed end (46).

20 Claims, 1 Drawing Sheet

(56) References Cited

U.S. PATENT DOCUMENTS

| | | | | |
|---|---|---|---|---|
| 5,947,667 | A * | 9/1999 | Cassatt | F16B 19/1063 411/34 |
| 6,338,747 | B1 * | 1/2002 | Kosco | C22C 33/02 419/11 |
| 6,406,560 | B1 * | 6/2002 | Lerche | C23C 8/32 148/216 |
| 6,537,004 | B2 * | 3/2003 | Cosenza | F16B 5/02 411/286 |
| 6,547,500 | B2 * | 4/2003 | Cosenza | F16B 5/02 411/34 |
| 6,547,888 | B1 * | 4/2003 | Williams | C23C 8/22 148/206 |
| 6,676,347 | B2 * | 1/2004 | Jensen | F16B 5/02 411/284 |
| 8,393,226 | B2 * | 3/2013 | Fujita | G01N 3/08 73/826 |
| 2005/0173026 | A1 * | 8/2005 | Taniguchi | C23C 8/80 148/233 |
| 2006/0058843 | A1 * | 3/2006 | Mashiko | A61B 17/06066 606/222 |
| 2012/0063945 | A1 * | 3/2012 | Tsuchida | C22C 38/001 420/93 |
| 2012/0082586 | A1 * | 4/2012 | Moyer | C23C 8/34 419/13 |
| 2012/0111454 | A1 * | 5/2012 | Moyer | C23C 8/22 148/207 |
| 2014/0236237 | A1 * | 8/2014 | Mahajan | A61B 17/863 606/270 |

OTHER PUBLICATIONS

ASTM E606 "Standard Test Method for Strain-Controlled Fatigue Testing", ASTM International, West Conshohocken, Pennsylvania, 2005, DOI: 10.1520/E0606_E0606M-12, pp. 681-698.

Brochure: INSTRON 8801 Servohydraulic Fatigue Testing System, Illinois Tool Works, Inc., Norwood, Massachusetts, 2012.

* cited by examiner

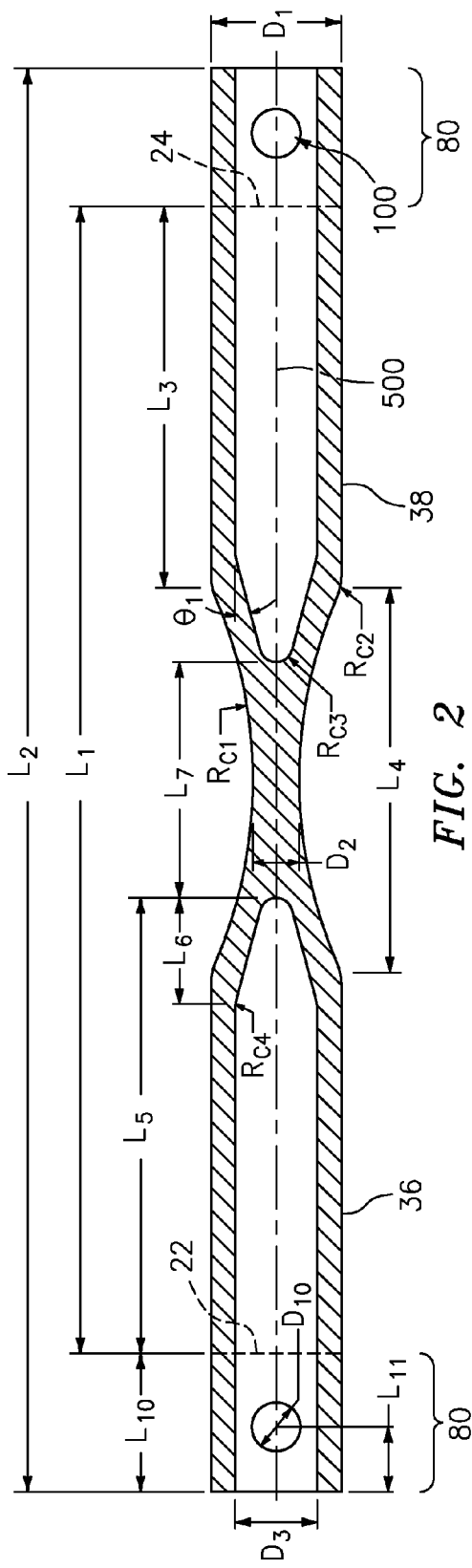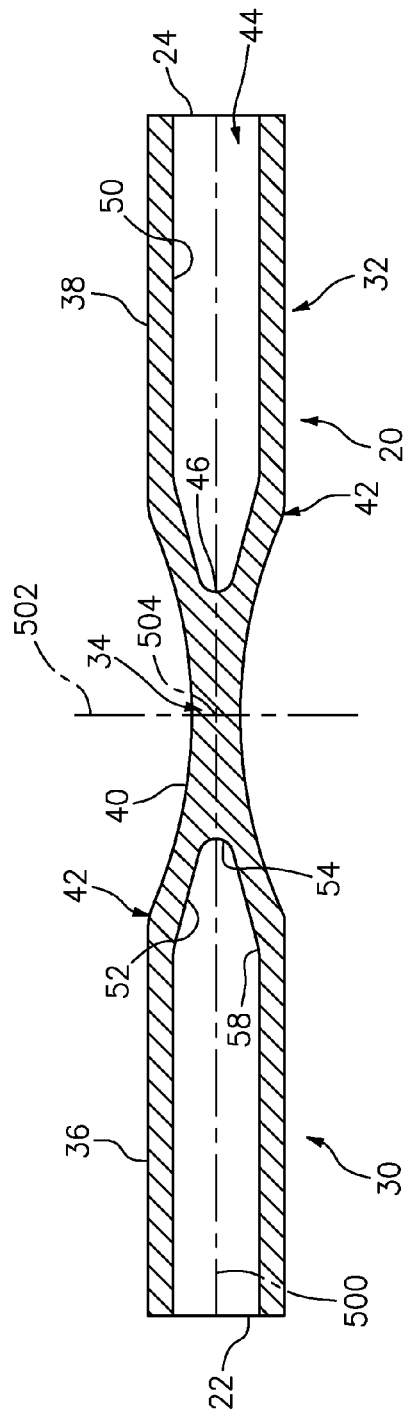

FATIGUE TEST SPECIMEN

CROSS-REFERENCE TO RELATED APPLICATION

Benefit is claimed of U.S. Patent Application Ser. No. 61/777,351, filed Mar. 12, 2013, and entitled "Fatigue Test Specimen", the disclosure of which is incorporated by reference herein in its entirety as if set forth at length.

BACKGROUND

The disclosure relates to materials testing. More particularly, the disclosure relates to axial fatigue test specimens.

A well-developed field exists in fatigue testing of material such as metal alloys. An exemplary axial fatigue test specimen is formed as a solid body of revolution having first and second end portions for mounting in a test equipment and a narrowed intermediate gauge portion. The narrowing of the gauge portion will localize failure to the gauge portion and isolate the failures from effects of gripping by the test equipment.

Exemplary specimens and test procedures are found in ASTM E606 "Standard Test Method for Strain-Controlled Fatigue Testing", ASTM International, West Conshohocken, Pa., 2005, DOI: 10.1520/E0606_E0606M-12. Among examples of test equipment are those sold under the INSTRON brand by Illinois Tool Works, Inc., Norwood, Mass. Exemplary test equipment is used to place a static or cyclic load on the test specimen. Measurements may be made of strained deformation, loads (e.g., failure loads or relationships between loads and deformations), and the like.

SUMMARY

Accordingly, one aspect of disclosure involves a metallic test specimen extending along a central longitudinal axis between a first end and a second end. The specimen has a first mounting section and a section mounting section. A narrowed gauge section is between the first mounting section and the second mounting section. The first mounting section and the second mounting section each have a blind compartment extending longitudinally inward to a closed end.

In one or more embodiments of any of the foregoing embodiments, the test specimen may be formed of steel. The steel may be carburized. The steel may be a stainless steel.

In one or more embodiments of any of the foregoing embodiments, at least the gauge section may be formed as a body of revolution about the central longitudinal axis. At least the gauge section may be symmetric across a transverse centerplane. An external contour of a majority of a length of the gauge section may be concave in longitudinal section. An external contour of a majority of a length of the mounting sections may be cylindrical.

In one or more embodiments of any of the foregoing embodiments, the closed ends may be convergent and may be rounded. The closed ends may be within the gauge section. A separation between the closed ends may be at least 10% of an overall length of the test specimen.

Another aspect of the disclosure involves a method for manufacturing the test specimen. The method includes forming the compartments and a lateral external contour. The method includes, after the forming of the compartments, carburizing.

In one or more embodiments of any of the foregoing methods, the compartments and a lateral external contour may be formed on a precursor longer than the test specimens. After the carburizing, end portions may be removed from the precursor to leave the first and second ends.

In one or more embodiments of any of the foregoing embodiments, the precursor end portions may have transverse holes. The transverse holes may used to suspend the precursor. The transverse holes may used to suspend the precursor during heating or quenching.

In one or more embodiments of any of the foregoing embodiments, the carburization may comprise heating in an atmosphere of 0.8-1.6% of carbon by volume.

In one or more embodiments of any of the foregoing embodiments, there may a multiple-cycle heat treatment with alternating heating and liquid nitrogen quenching.

In one or more embodiments of any of the foregoing embodiments, the specimen may be mounted in a test apparatus. The test apparatus may be used to apply a load across the gauge section. The load may be a cyclic load. The test may involve measuring one or more of a displacement or a time to failure. The load may represent a failure load.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 1 is a longitudinal sectional view of a specimen.
FIG. 2 is a longitudinal sectional view of a precursor of the specimen of FIG. 1.
Like reference numbers and designations in the various drawings indicate like elements.

DETAILED DESCRIPTION

FIG. 1 shows a test specimen 20. The exemplary specimen 20 comprises a single metallic piece extending along a central longitudinal axis 500 between a first end 22 and a second end 24. FIG. 1 further shows a transverse centerplane 502 and a transverse central axis 504 (arbitrarily chosen as one of the infinite number of axes in the plane 502 intersecting the axis 500). The exemplary specimen is a stainless steel. The exemplary stainless steel is used for gear and bearing applications. As is discussed further below, the exemplary steel is subject to a carburization process prior to testing.

Proximate the first end 22 the specimen has a first mounting section 30 and proximate the second end 24 the specimen has a second mounting section 32. A narrowed gauge section 34 is between the first and second mounting sections. The exemplary mounting sections are straight sections for collet mounting. Alternative sections include threaded and button.

An external surface/contour/profile is characterized by a straight cylindrical portion 36, 38 along the respective first and second mounting sections and a concave (when viewed in longitudinal section) portion 40 along the gauge section. The sectional profile of the specimen may have radiused transitions 42 between opposite ends of the concave surface portion 40 and the adjacent inboard ends of the straight/cylindrical surface portions 36 and 38.

The exterior contour so far described and its exemplary dimensions discussed below may be identical to those of a baseline prior art specimen or may be modified. The specimen 20, however, has a pair of blind compartments 44 extending longitudinally inward within the respective mounting sections 30, 32 from the respective specimen ends 22, 24. The compartments are "blind" in that they do not fully penetrate the gauge section but rather terminate at a closed end 46. The exemplary compartments 44 are characterized by an inboard surface of the specimen facing radially inward and including a straight/cylindrical portion 50 extending inward from the associated specimen end 22, 24, a convergent portion 52 (e.g., generally conical) and a rounded end portion 54 at the end 46. The exemplary specimen includes a radiused transition 58 between the surface portions 50 and 52.

FIG. 2 shows a precursor of the specimen 20. The precursor includes end/terminal sections 80 as continuations of the mounting sections. These end sections 80 are relevant in the pre-test processing of the specimen as is discussed further below. These end sections 80 are removed prior to testing. FIG. 2 further shows an end-to-end specimen length as $L_1$ and an end-to-end precursor length as $L_2$. Sections 80 thus account for the difference, each having a length shown as $L_{10}$. FIG. 2 further shows a diameter $D_1$ along the cylindrical sections/surfaces 36, 38 and a diameter $D_2$ as the minimum diameter of the gauge section 34 (i.e., at the transverse centerplane 502). An overall length of each mounting section (from the end 22, 24 to the center of the associated transition 42) is shown as $L_3$. A similarly-measured length of the gauge section 34 between the transitions 42 is shown as $L_4$. A compartment depth (e.g., from the end 22, 24 to the associated end 46) is shown as $L_5$. A convergent end portion of the compartment formed by the surfaces 52 and 54 measured from the center of the transition 58 to the end 46 is shown as $L_6$. A diameter of cylindrical surface 50 is shown as $D_3$. A length of the solid/continuous portion of the center section between the ends 46 is shown as $L_7$. A half angle of convergence of the surface 52 is shown as $\theta_1$. The radius of curvature of the transition 42 is shown as $R_{C2}$. The radius of curvature of the end portion 54 is shown as $R_{C3}$. The radius of curvature of the transition 58 is shown as $R_{C4}$.

As is discussed further below, the exemplary proportions allow the compartments to extend fully through the mounting sections 30, 32 and partially into the gauge section. The angle $\theta_1$ is chosen to be sufficiently similar to a convergence angle along the adjacent inwardly converging surface 40 so that there is a relatively constant wall thickness. This allows relatively even exposure to carburization while still maintaining material strength in the mounting sections and the adjacent longitudinally outboard portions of the gauge section.

In terms of relative dimensions, exemplary $L_7$ is at least 10% of $L_1$, more particularly, 10-30% or 15-30%. Exemplary $L_1$ is at least 50% of $L_4$, more particularly, 50-80% or 60-75%. The exemplary $\theta_1$ is 10-40°, more particularly, 15-30°.

FIG. 2 further shows holes 100 in the end portions 80 having respective diameters shown as $D_{10}$ and centers spaced from the precursor ends by a distance $L_{11}$. In the exemplary embodiment, there are two such diametrically opposite holes in each end portion 80 whose use is discussed below. In some test equipment, the end portions 80 may be used as part of the mounting section with a fastener or other engagement into the holes 100 for retention. In other implementations, the end portions and their holes may merely provide convenient gripping or holding portions for performing various processing stages (carburization or other heat treatments discussed below and quenchings discussed below). For example, during such stages, the specimens may be externally gripped around the perimeter of the end portions 80 or may be suspended using hooks or the like passing through the holes 100. Alternatively, the end portions 80 may merely be gripping portions for machining and may be removed prior to carburization and heat treatment.

An exemplary sequence of manufacture for a low carbon alloy steel specimen starts with forming cylindrical precursor bars by vacuum induction melting and vacuum arc re-melting of initial bar stock. The precursors are then hot worked to pre-finish dimensions (e.g., within 0.12 inch (3.0 mm) surface thickness of the minimum cylindrical envelope for further processing). Then, the outer diameter (OD) surface is ground to produce a suitable surface finish for inspection (e.g., immersion ultrasonic testing). This may involve the removal of an exemplary 0.010-0.030 inch (radially) (0.25-0.76 mm) of material.

The specimens may then be cleaned and inspected (immersion ultrasonic tested) to check for material defects such as inclusions or voids. Specimens that pass such inspection may then be rough machined externally and internally. The external/outer diameter (OD) surface may be machined using a lathe; the internal surfaces of the compartments may be machined using a ball end mill. The lateral holes 100 may be drilled either before or after such machining. These steps may result in an exemplary semi-finished dimension (e.g., 0.015-0.030 inch (radially) (0.38-0.76 mm) out of the final hourglass shape).

A carburization cycle may then be performed in a furnace chamber. An exemplary cycle is performed at elevated temperatures and carbon level (e.g., 1700° F. (927° C.) and 0.9% elemental carbon by volume). The exemplary cycle may last more than day (e.g., an exemplary 75 hours). The chamber may then be cooled (e.g., to 300° F. (149° C.)) whereupon the specimen is removed. Carburization results in a case hardening of the specimen. Exemplary carburization is at a minimum temperature of 1250° F. (677° C.), more narrowly, 1600° F.-1800° F. (871° C.-982° C.). The exemplary carbon environment is at least 0.6% by volume, more narrowly, 0.8%-1.6%. The exemplary duration is a minimum of thirty hours, more narrowly, 50-150 hours. In alternative possibilities, other parameters might merely be effective to produce similar carburization.

Exemplary carbon levels after all processing below involves a distribution of carbon with peak values at the surface. Exemplary peak values at the surface are approximately 0.895% by weight with minimum interior values of approximately 0.13%. More broadly, the surface may peak at up to an exemplary 1.5% carbon (by weight) while the interior may be at as low as an exemplary 0.005%. The exemplary processing is effective to raise surface carbon by an amount of at least an exemplary 0.5%, more particularly, at least 0.7% or an exemplary 0.8-1.0% by weight.

After carburization, an annealing cycle may be performed. Exemplary annealing is for a period of only several hours, in an elevated carbon environment but at a lesser temperature than the carburization. Exemplary annealing is at 1350° F. (732° C.) and 0.75% carbon for three hours. Again the chamber is then cooled to (e.g., 350° F. (177° C.)) whereupon the specimen is removed. Annealing puts the carbon into solution to meet required microstructure requirements for the particular alloy. Exemplary anneal is at a minimum temperature of 1100° F. (593° C.), more narrowly, 1250° F.-1500° F. (677° C.-816° C.). Typical carbon content during anneal is 0.5% minimum by weight, more narrowly, 0.65%-1.0%. Exemplary anneal time is one hour minimum, more narrowly, two hours to five hours.

The specimens may then be further hardened in a heat treatment furnace. In the exemplary embodiment this is at an intermediate temperature and for a relative short duration (in a carbon-rich environment (e.g., 1525° F. (829° C.), 0.9% carbon dioxide, 1.25 hours)). The specimens are then promptly oil quenched (e.g., at 120° F. (49° C.)). The quenching cycle converts a mostly austenitic microstructure to a mostly martensitic microstructure. Exemplary hardening is at a minimum temperature of 1300° F. (704° C.), more narrowly, 1400° F.-1650° F. (706° C.-899° C.). Exemplary minimum carbon content during hardening is 0.6% min, more narrowly, 0.8%-1.6%. Exemplary hardening time is 0.5 hours min, more narrowly, 0.75-2.5 hours.

After the quenching, a triple tempering may be performed to minimize any retained austenite in the material. Exemplary triple tempering involves three cycles using a heat treatment furnace followed by a liquid nitrogen cryogenic tank quench with the heating at 300° F. (149° C.) for two hours. Exemplary tempering is at a minimum temperature of 200° F. (93° C.), more narrowly, 250° F.-400° F. (121° C.-204° C.). Exemplary tempering time is a minimum of one hour, more narrowly, 1.5 hours to five hours.

After the tempering, the specimen may then be finish machined on its interior and exterior surfaces using grinding equipment.

In an exemplary embodiment, $D_2$ is 0.175+/−0.001 inch (4.445+/−0.025 mm). $D_1$ is 0.500+/−0.001 inch (1.270+/−0.025 mm). These represent one of several possible standard test specimens. Exemplary $L_2$ is 4.41+/−0.01 inch (112.01+/−0.25 mm). Exemplary $L_2$ is 5.47+/−0.05 inch (138.9+/−1.3 mm). Exemplary $R_{C1}$ is 1.75+/−0.01 inch (44.45+/−0.25 mm). Exemplary $L_5$ is 1.75+/−0.01 inch. Exemplary $D_3$ is 0.312+/−0.002 inch (7.92+/−0.05 mm). Exemplary $\theta_1$ is 15°. Exemplary $R_{C3}$ is 0.062 inch (1.6 mm). The interior dimensions may have greater flexibility for a given standard specimen wherein certain exterior (e.g., outer diameter) dimensions may be dictated by the test machine or industry practice. As noted above, alternative test apparatus may require the OD surfaces of the end portions to be threaded or have annular rims or "buttons" for securing to the test apparatus. In various other potential apparatus, exemplary $D_1$ may, more broadly, be 1-4 cm and exemplary $D_2$ may be 20-50% of $D_1$. Exemplary overall specimen length may be 8-30 cm.

Exemplary testing may be a cyclical tensile test with the mounting portions gripped by the test apparatus. The apparatus supplies known cyclical force/load and measures displacements and time to failure. Torsional or bending tests may alternatively be performed.

In at least some implementations, the presence of the compartments and the resulting interior carburization may avoid specimen failures outside of the gauge section. This may improve the accuracy and representative quality of the test.

Although an embodiment is described above in detail, such description is not intended for limiting the scope of the present disclosure. It will be understood that various modifications may be made without departing from the spirit and scope of the disclosure. For example, when applied in the modification of baseline specimens or for use with a given baseline piece of test equipment, details of such baseline may influence details of any particular implementation. Accordingly, other embodiments are within the scope of the following claims.

What is claimed is:

1. A metallic test specimen (20) extending along a central longitudinal axis (500) between a first end (22) and a second end (24) and comprising:
   a first mounting section (30);
   a second mounting section (32); and
   a narrowed gauge section (34) between the first mounting section and the second mounting section, wherein:
      the test specimen is formed of steel; and
      the first mounting section and the second mounting section each have a blind compartment (44) extending longitudinally inward to a closed end (46).

2. The test specimen of claim 1 wherein the steel is carburized.

3. The test specimen of claim 1 wherein the steel is stainless steel.

4. The test specimen of claim 1 wherein at least the gauge section is formed as a body of revolution about the central longitudinal axis (500).

5. The test specimen of claim 1 wherein at least the gauge section (34) is symmetric across a transverse centerplane (502).

6. The test specimen of claim 1 wherein:
   an external contour of a majority of a length of the gauge section is concave (40) in longitudinal section.

7. The test specimen of claim 1 wherein:
   an external contour of a majority of a length of the mounting sections is cylindrical (38).

8. The test specimen of claim 1 wherein:
   the closed ends are within the gauge section.

9. The test specimen of claim 1 wherein:
   a separation between the closed ends is at least 10% of an overall length of the test specimen.

10. A method for manufacturing the test specimen of claim 1, the method comprising:
    forming the compartments and a lateral external contour; and
    after the forming of the compartments, carburizing.

11. The method of claim 10 wherein:
    the forming of the compartments and a lateral external contour are on a precursor longer than the test specimens; and
    after the carburizing, end portions are removed from the precursor to leave the first and second ends.

12. The method of claim 11 wherein:
    the precursor end portions have transverse holes which are used to suspend the precursor.

13. The method of claim 10 wherein:
    the carburizing comprises heating in an atmosphere of 0.8-1.6% of carbon by volume.

14. The method of claim 10 further comprises:
    one or more heat treatment cycles of heating followed by liquid nitrogen quenching.

15. A metallic test specimen (20) extending along a central longitudinal axis (500) between a first end (22) and a second end (24) and comprising:
    a first mounting section (30);
    a second mounting section (32); and
    a narrowed gauge section (34) between the first mounting section and the second mounting section,
    wherein:
    the first mounting section and the second mounting section each have a blind
    compartment (44) extending longitudinally inward to a closed end (46); and
    the closed ends are convergent and rounded.

16. A method for using a metallic test specimen (20), the metallic test specimen extending along a central longitudinal axis (500) between a first end (22) and a second end (24) and comprising:
    a first mounting section (30);
    a second mounting section (32); and
    a narrowed gauge section (34) between the first mounting section and the second mounting section,
    wherein:
       the first mounting section and the second mounting section each have a blind compartment (44) extending longitudinally inward to a closed end (46),
    the method comprising:
       mounting the specimen in a test apparatus; and using the test apparatus to apply a load across the gauge section.

17. The method of claim 16 wherein:
the load is cyclically applied.

18. The method of claim 16 wherein:
a measurement is made of a displacement and/or a time to failure.

19. The method of claim 16 wherein at least the gauge section is formed as a body of revolution about the central longitudinal axis (500).

20. The method of claim 19 wherein an external contour of a majority of a length of the gauge section is concave (40) in a longitudinal section.

* * * * *